United States Patent [19]

Mohajer

[11] Patent Number: 4,821,741
[45] Date of Patent: Apr. 18, 1989

[54] BARRIER CONTRACEPTIVE

[76] Inventor: Reza S. Mohajer, 1275 Orchard Ridge Rd., Bloomfield Hills, Mich. 48013

[21] Appl. No.: 104,428

[22] Filed: Oct. 5, 1987

Related U.S. Application Data

[63] Continuation-in-part of Ser. No. 37,212, Apr. 10, 1987.

[51] Int. Cl.⁴ .................................................. A61F 5/46
[52] U.S. Cl. .................................... 128/837; 128/832; 128/840
[58] Field of Search ................ 128/127, 130, 131; 604/48, 55, 93

[56] References Cited

U.S. PATENT DOCUMENTS

| | | | |
|---|---|---|---|
| 2,391,343 | 12/1945 | Popper | 128/127 |
| 2,580,133 | 12/1951 | Sheen | 128/127 |
| 2,836,177 | 5/1958 | Sells | 128/127 |
| 3,130,721 | 4/1964 | Young | 128/127 |
| 3,371,664 | 3/1968 | Pleshette | 128/127 |
| 3,845,766 | 11/1974 | Zöller | 128/127 |
| 4,198,976 | 4/1980 | Drobish et al. | 128/131 |
| 4,286,593 | 9/1981 | Place et al. | 128/127 |
| 4,304,226 | 12/1981 | Drobish et al. | 604/55 |
| 4,320,751 | 3/1982 | Loeb | 128/127 |
| 4,369,219 | 1/1983 | Goepp et al. | 128/127 |
| 4,369,773 | 1/1983 | Chvapil | 128/127 |
| 4,393,871 | 7/1983 | Vorhauer et al. | 604/55 |
| 4,553,965 | 11/1985 | Conn et al. | 604/55 |
| 4,696,294 | 9/1987 | Reyner | 128/131 |
| 4,703,752 | 11/1987 | Gabbay | 128/127 |

Primary Examiner—Robert A. Hafer
Assistant Examiner—Charles H. Sam
Attorney, Agent, or Firm—Krass & Young

[57] ABSTRACT

A barrier type contraceptive is an umbrella-like device including a flexible, barrier member with a plurality of radially disposed resilient stiffening members associated therewith. The stiffening members bias the barrier member into a generally planar configuration while allowing for the device to be folded into a generally fusiform shape for insertion.

1 Claim, 4 Drawing Sheets

BARRIER CONTRACEPTIVE

RELATED APPLICATION

This is a continuation-in-part of U.S. Pat. application of Ser. No. 037,212; filed Apr. 10, 1987.

FIELD OF THE INVENTION

This invention relates generally to contraceptive devices and in particular to barrier contraceptive devices of the diaphragm type.

BACKGROUND OF THE INVENTION

Control of conception has been an important medical endeavor for many years and instructions for the manufacture of contraceptive devices and compositions are found in some of the earliest known medical manuscripts. Presently, contraceptive technologies rely upon pharmaceutical and mechanical methods. Pharmaceutical methods involve the use of medicinal compounds which prevent pregnancy by interfering with ovulation, implantation or spermatogenesis. Mechanical methods are directed to preventing contact of ovum and sperm and involve the use of mechanical barriers and spermicidal compounds.

Because of the increasing concern with the side effects of pharmaceutical compositions, mechanical methods of contraception are increasing in popularity. Additionally, concern with sexually transmitted diseases has engendered a renewed interest in barrier type devices.

The cervical cap is one of the earliest types of mechanical contraceptives available, having been introduced over 150 years ago. The cervical cap is a generally rigid, relatively small device fitted directly onto the cervix where it forms a barrier to the passage of spermatozoa thereinto. Although the cervical cap has been available for a relatively long period of time it is of rather limited use. In order to obtain a good fit, it is generally required that wax or latex impressions of the cervix be taken and these impressions utilized to fabricate a custom fitted cap. Such fitting is expensive, time consuming and requires the assistance of highly trained personnel. Insertion and removal of the cervical cap is relatively difficult and frequently must be done by trained personnel. The cap is generally left in place for relatively long periods of time and this placement can encourage undesired side effects such as the growth of anaerobic bacteria in the uterus, toxic shock syndrome and mechanical damage such as cervical erosion. Such technology is described in U.S. Pat. Nos. 4,517,970; 4,401,534 and 4,467,789.

A more commonly utilized type of barrier contraceptive is the diaphragm, which has been available since the end of the 19th Century and which has been in relatively wise use in the last thirty years. The diaphragm presently utilizes is generally similar in design to that first invented in 1882 by Dr. C. Hasse. It is comprised of a flexible rubber barrier of generally circular shape having a rigid, thickened rim reinforced with a metal spring. In use, the diaphragm is inserted in the vagina so that it forms a barrier seal protecting the opening of the cervix.

While presently utilized diaphragms are quite well accepted, use of such devices is not without problems. The proper fitting of diaphragms is essential if reliable contraception is to be obtained. The diaphragm must contact the vaginal wall uniformly and tightly so as to prevent spermatozoa from passing therearound. Accordingly, presently available contraceptive diaphragms are provided in a wide range of sizes and must be fitted carefully by trained medical personnel. Additionally, the user must be trained in proper methods of insertion if the function of the diaphragm is to be reliable. An improperly fitted, or improperly inserted diaphragm may become dislodged during sexual activity thereby permitting conception to occur.

Since proper fit is so crucial to diaphragm function, women utilizing such devices should be carefully monitored. If a weight gain or loss of more than 15 pounds occurs it is generally advised that the diaphragm be refitted. Similarly, child birth, abdominal surgery or other such events will necessitate refitting of a contraceptive diaphragm. The rigid rim of such diaphragms can cause problems with its use. Many women cannot tolerate such a device because of the size or shape of their vaginal walls or cervix. In addition, the rigid rim can in some instances cause pressure ulceration to occur. Accordingly, it will be appreciated that there is a need for a device which eliminates these shortcomings of the presently available diaphragm.

Contraceptive sponges are another class of devices enjoying increasing popularity. The contraceptive sponge is a generally flattened, cylindrical device made of resilient polyurethane foam or similar materials impregnated with a spermicidal compound. Such a device is not strictly speaking a barrier insofar as it does not impose any impenetrable cover over the cervix. Instead, it is believed that the contraceptive sponge functions by spermicidal action. The contraceptive sponge need not be custom fitted for individual users and accordingly may be purchased over the counter without prescription, and for this reason is enjoying widespread use. The contraceptive sponge is not without shortcomings however. In general the contraceptive sponge has a lower reliability rate than does a properly fitted diaphragm. Problems occur because of dislodgement of the device, bypass of the device or ineffectiveness of the spermicide. Dislodgement and bypass can occur during sexual activity when the penis moves past the sponge pushing it away from the cervix. Ejaculation can then occur in the vicinity of the cervix and spermatozoa can pass thereinto without being exposed to the spermicidal compound in the sponge.

In addition to problems of reliability, there are also problems of a mechanical nature involved in the use of contraceptive sponges. In many instances, users have found it difficult to remove such sponges from the vaginal cavity. In those cases, the sponge tears or breaks thereby preventing removal, and medical assistance must be resorted to remove all traces of the sponge. In other instances, the use of contraceptive sponges has been associated with toxic shock syndrome. Some women also have problems retaining the sponge for a sufficient length of time to insure contraception.

Accordingly, it will be appreciated that there is a need for a contraceptive device which enjoys the reliability and general safety of heretofore employed contraceptive diaphragms and which has the additional advantages of presently utilized contraceptive sponges insofar as it eliminates the need for fitting by trained personnel. Such a contraceptive device could readily be sold over the counter in one or two basic sizes to accommodate most women. It may be preferable in some instances to fabricate such devices as one time disposable items whereas in other instances a reusable contraceptive of this type will be desired. It is further desired that such contraceptive devices be relatively easy to insert and remove and that they have sufficient flexibility so as to prevent the formation of ulcers or erosions.

The present invention provides for a barrier type contraceptive fulfilling these needs. The contraceptive of the present invention is a generally umbrella shaped article which may be readily folded into an elongated or fusiform shape for insertion or removal. Once in place, the contraceptive device of the present invention is adapted to expand so as to uniformly contact the vaginal walls thereby forming a tight barrier seal. The contraceptive of the present invention may be utilized in conjunction with spermicidal compounds and may further include reservoirs for such compounds as well as a handle or loop for removal. In addition to being utilized as a contraceptive device, the umbrella-like diaphragm of the present invention may be utilized as a therapeutic device adapted to release medicinal compounds into the vaginal environment. These and other advantages and features of the present invention will be readily apparent from the summary, drawings, detailed description and claims which follow.

BRIEF DESCRIPTION OF THE INVENTION

There is disclosed herein a barrier-type contraceptive comprised of a flexible barrier member having a plurality of radially disposed resilient stiffening members associated therewith. These stiffening members are adapted to bias the barrier member into a generally planar configuration. Additionally, the stiffening members have sufficient flexibility to allow the device to be folded into a generally fusiform shape. In one particular embodiment, the stiffening members are joined together proximate the center of the barrier so as to provide sufficient biasing force, whereas in other instances the stiffening members are joined together at a point eccentric with respect to the barrier member. The stiffening members may be formed from a wide variety of materials as for example; metal, synthetic polymers, natural rubber and various combinations thereof. The stiffening members may be embedded in the barrier member or laminated between two sheets of barrier member material so as to be completely encapsulated thereby or they may be affixed to at least one surface of the barrier member. In one specific embodiment, the stiffening members are made of the same material as the flexible barrier member and are provided by the thickened portions thereof. In other instances it may be desirable to form the stiffening member so as to be relatively thick proximate the center of the barrier member and relatively thin proximate the perimeter thereof.

The flexible barrier member may be fabricated from a wide variety of materials such as; natural rubber, synthetic rubber, silicone rubber and synthetic polymeric materials. One material having particular utility for the fabrication of barrier and/or stiffening members is a copolymer of a terepthalate polyester and a polyether glycol.

In one embodiment, the barrier member is a generally conical member having a circular perimeter and may for example have a diameter of approximately 55-95 millimeters. In other instances the barrier member has an oval perimeter. The conical barrier member is preferably formed from an elastic material and the stiffeners cooperate with the elastic material so as to allow for an increase in the size of the perimeter of the barrier as the conical height thereof is decreased. In this manner, the device is adapted to uniformly contact its circular perimeter to the vaginal wall.

The flexible barrier member may be configured so as to include a reservoir adapted to hold and selectively release a medicinal compound therefrom. Additionally, the device may include a handle configured so as to facilitate withdrawal thereof, as well as tactile placement indicia. The present invention also includes a generally tube-like inserter adapted to retain the folded device therein for insertion into the vaginal canal.

In one specific embodiment, a barrier contraceptive includes two flexible, generally conical barrier members each having a circular perimeter and being joined at a plurality of points along those circular perimeters. At least one of the barrier members may include a plurality of radially disposed, resilient stiffener members associated therewith and adapted to bias the barrier members into a generally planar configuration while allowing the device to be folded into a fusiform shape. A device of this particular configuration is particularly well suited for containing a medicinal compound such as a spermicidal or therapeutic compound therein.

DETAILED DESCRIPTION OF THE INVENTION

Figure 1:
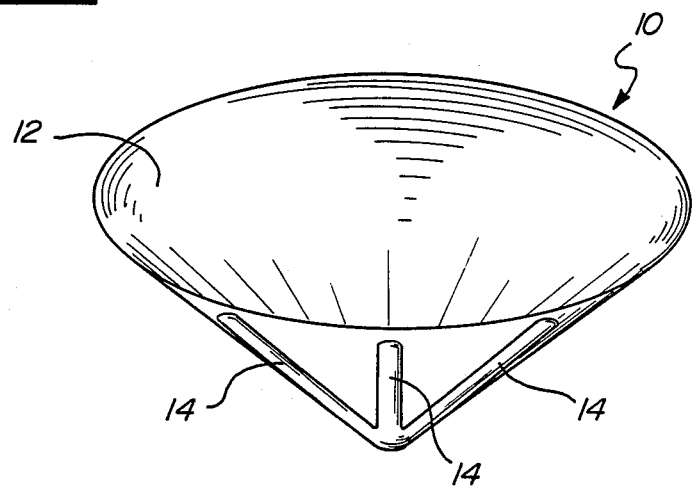
FIG. 1 is a perspective view of a particular barrier contraceptive device fabricated in accord with the principles of the present invention.

Referring now to FIG. 1, there is shown a first embodiment of barrier-type contraceptive structured in accord with the principles of the instant invention. The device 10 of FIG. 1, is a generally umbrella-like device generally comprised of a flexible barrier member 12, which in this embodiment is structured as a conical member having a circular perimeter. Included in the device 10 are a plurality of stiffening members 14 which are adapted to bias the conical barrier member into a generally planar configuration. As shown in FIG. 1, the contraceptive device 10 is shown as biased into what is referred to herein as "a generally planar configuration," and it will be appreciated that said planar configuration includes the conical or open umbrella-shaped configuration illustrated with reference to FIG. 1.

In addition to biasing the barrier member 12 into a planar configuration, the stiffening members 14 also have sufficient flexibility so as to allow the device 10 to be folded into a generally fusiform shape for insertion.

Figure 3:
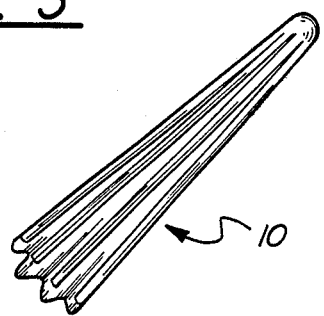
FIG. 3 is a perspective view of the device of FIGS. 1 and 2 as folded into a fusiform shape.

Referring now to FIG. 3, there is shown a folded form of the contraceptive device 10 of the present invention. By "fusiform" is meant a generally elongated or cylindrical shape substantially as shown with reference to FIG. 3.

Figure 2:
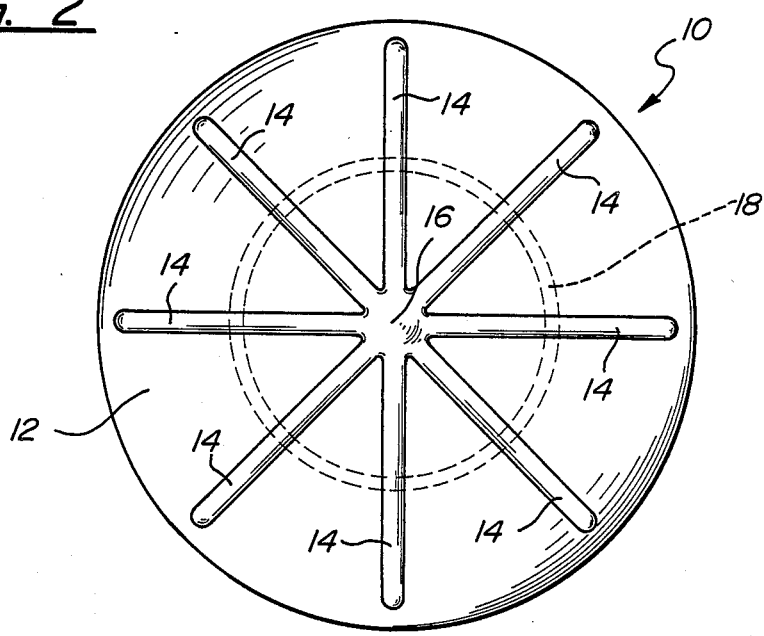
FIG. 2 is a top plan view of the device of FIG. 1.

Referring now to FIG. 2, there is shown a top plan view of the barrier contraceptive 10 of the present invention illustrating one particular embodiment of stiffening member configuration. As it will be seen from the figure, stiffening members 4 are interconnected at a common locus 16, proximate the center of the barrier member 12. Also, as illustrated, the barrier contraceptive 10 includes 8 stiffening members 14.

It will be appreciated that other configurations of stiffening member may be utilized in conjunction with the present invention. For example, a larger of smaller number of stiffening members may be utilized and those members may be joined in other manners. For example, the stiffening members 14 may fasten to a ring-like member generally encircling the central portion of the barrier member 12. Alternatively, the stiffening members 14 may not all be joined at a central locus. For example, one or two pairs of the stiffening members may join at the central region whereas others may be unattached members. Furthermore, in addition to being interconnected at a central portion, the stiffening members 14 may be additionally interconnected at various other points along the length thereof so as to form a web-like pattern. In yet other embodiments, the stiffening members 14 may be additionally encircled by a circular stiffening member 18 (shown in phantom outline herein) adapted to aid in biasing the barrier contraceptive 10 into a deployed, substantially planar configuration. The stiffening members may be disposed upon either surface of the barrier member 12, or they may be embedded within the barrier member 12, itself.

In use, the barrier contraceptive device 10 is folded into the generally fusiform shape illustrated in FIG. 3 and inserted into the vagina. The stiffening members 14 cooperate to expand the folded device 10 in a manner similar to the opening of an umbrella. Because of the flexibility of the barrier member 12 and the biasing force of the stiffening members 14 the device 10 expands until uniform contact with the vaginal walls is attained thereby forming a tight barrier. The fact that the expansion and contact is maintained by the stiffening members 14 allows for the fabrication of a device 10 having a relatively soft perimeter which thereby avoids the danger of pressure ulceration and the like heretofore encountered with spring rim diaphragms.

The use of such a design confers additional advantages in contraceptive reliability insofar as pressure upon the face of the barrier contraceptive device occurring during sexual intercourse will tend to further bias the device into a planar configuration so as to tighten the seal thereof. In this manner, the tightest seal is achieved at the time of ejaculation, when such seal is most critical. It should be readily appreciated that the generally umbrella-like configuration of the barrier contraceptive disclosed herein further allows for ease of removal of the device insofar as it will readily fold back to the closed configuration when withdrawn.

The fact that the umbrella-like device disclosed herein expands to accomodate various sizes of user is a very important feature insofar as it obviates the need to employ trained personnel for custom fitting of diaphragm-type devices as well as the need for dispensers to stock multiple sizes. It is anticipated that a diameter of approximately 55-95 millimeters for the expanded device, as measured across the circular perimeter thereof, should be sufficient to accomodate the majority of women. Umbrella-type barrier contraceptive devices may be fabricated in two size ranges, a first range capable of expanding to diameters of 50-75 millimeters, and a second size adapted to expand from 70-95 millimeters. It is further anticipated that the devices of the present invention may be manufactured in a single size adapted to be cut by the dispenser, or end user so as to achieve the proper size range. For example, the surface of the flexible barrier 12, may be marked with a line indicating where the device should be cut so as to provide a proper sizing.

The fact that the umbrella type devices of the present invention need not be custom fitted readily adapts their use for direct over the counter sales to consumers and further suits such devices for use in developing countries where trained personnel are not readily available. The device of the present invention may be fabricated as a reusable device or may be a single service item.

The umbrella-like barrier contraceptive functions quite well to prevent pregnancy, however it may utilized in combination with spermicidal compounds to further increase the efficiency thereof in a manner analogous to the use of spermicides with heretofore available spring rim diaphrams. For example, spermicidal compositions may be placed within the conical portion of the flexible barrier 12 prior to insertion; and similarly, such compounds may be placed along the periphery of the device. When the barrier device 10 is folded into the fusiform shape, the spermicidal compound will be retained therein.

The flexibility of the present device further enhances the efficiency of utilization of spermicidal compounds insofar as pressure upon the face of the device, as transmitted by the stiffening members 14 will tend to push any spermicidal compound retained therein onto the subjacent cervix and along to the periphery of the device further enhancing the seal and forming a strong barrier to passage of spermatozoa. In order to accommodate the use of such compounds, the barrier device may be further modified to include reservoirs and the like, and such modifications will be described in greater detail hereinbelow.

In addition to the use of spermicidal compounds, other medications may be employed in conjunction with a device of the present invention. For example, the therapeutic agent 5 Flouro-uracil is utilized as an antichondyloma compound and such an agent may be placed in a device such as that illustrated herein, which device will then retain the chemotherapeutic agent in contact with the subjacent tissues. Similarly, agents for treating cervicitis and similar conditions may be employed. Also antiviral compounds, such as those compositions for preventing herpes or AIDs infection may be similarly utilized.

There are a wide variety of materials which may be utilized in the fabrication of the umbrella-like devices of the present invention. The barrier is advantageously fabricated from a flexible material having some degree of resiliency. Among such materials are natural rubber, silicone rubber, other synthetic rubbers, and various synthetic polymeric materials. The stiffening members are preferably thin, flexible members and may be fabricated from a variety of materials. Thin metal strips may be advantageously employed, as may be coiled or otherwise spring-like members. There are a wide variety of polymeric materials having a high degree of flexibility and resiliency and such materials may be advantageously employed to fabricate the stiffeners. For example fluorocarbon polymrs may be fabricated into spring-like strips adapted to function as stiffening members as may be nylon, polyester, polystyrene, polyvinylacetate and the like.

It has been found that elastomeric materials are advantageous in fabricating the devices of the present invention. Synthetic elastomers, such as polyester elastomers have been found to be of particular advantage insofar as their physical properties (e.g.; hardness, resiliency and melting point) can be readily controlled over a wide range.

A particularly advantageous material is a block copolymer of a terepthalate polyester and a long chain polyether glycol. One such commercially available material is a block copolymer consisting of a hard (crystalline) segment of polybutylene terepthalate and a soft (amorphous) segment based on long chain polyether glycols. Such materials are sold by the Dupont Corporation under the trade name Hytrel *. The physical properties of these polymers are determined by the ratio of hard to soft segments, as well as the makeup of the segments. Additionally, these materials are readily fabricated into finished shapes by common techniques such as compression molding.

By control of the previously mentioned parameters these polymers can be made relatively soft to enable their use in the fabrication of the barrier member; or, they can be made hard and resilient so as to be suitable for use as stiffening members. Hytrel * polymers are available in FDA approved food grades and it has been found that grade 4059FG, having a durometer hardness of 40, a flexural modulus of 55 MPa at 23° C. and a melting point of 195° C. is particularly well suited for the fabrication of barrier members; and grade 6359FG having a durometer hardness of 63, a flexural modulus of 300 MPa at 23° C. and a melting point of 213° C. is particularly well suited for the fabrication of stiffening members. It is to be understood however, that other grades of Hytrel *, as well as other polymers having similar properties may likewise be employed.

Use of various polymeric materials or the fabrication of the barrier contraceptive of the present invention confers an advantage insofar as such materials allow for ready cutting therethrough so as to permit the adjustment of the size of the resultant device. In some instances it may be advantageous to utilize a combination of materials to fabricate the stiffening members. For example, the members may be fabricated as strips of polymeric material circled by a metallic coil spring, as for example 18 in FIG. 1. In yet other instances, the stiffening members may be provided by thickened portions of the barrier member itself, as for example by molding in a plurality of ribs. All of such variations should be readily apparent to one of skill in the art.

The umbrella-like barrier contraceptive of the present invention may further include an inserter adapted to facilitate the use thereof.

Figure 4:
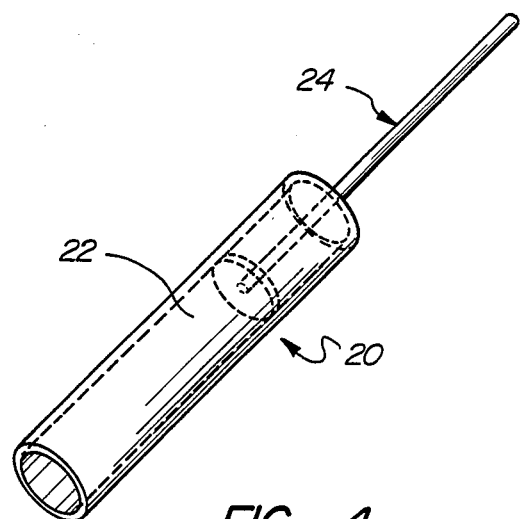
FIG. 4 is a drawing of one particular insertion device as adapted to insert the barrier contraceptive device of the present invention into the vaginal cavity.

Referring now to FIG. 4, there is shown one configuration of insertion device 20 as adapted to be used in the present invention. The inserter 20 is comprised of a generally tubular housing 22 adapted to retain the umbrella-like device of the present invention in its folded form. The tubular member 22 has a plunger 24 disposed in one end thereof and adapted to eject the folded barrier device therefrom. Obviously, other configurations of inserter may be similarly employed.

Figure 6:
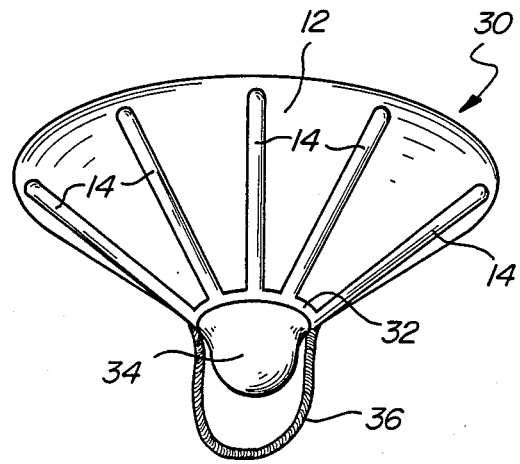
FIG. 6 is a perspective view of yet another barrier contraceptive device of the present invention.

Referring now to FIG. 6 there is shown yet another umbrella-like contraceptive device 30 structured in accord with the principles disclosed herein. The device 30 of FIG. 6 is generally similar to that disclosed with reference to FIG. 1 with the exception that the stiffening members 14 are not interconnected proximate the apex of the barrier member 12, but rather are attached to a ringlike portion 32 generally encircling the apex of the conical barrier member 12. The ringlike member 32 allows for the stiffening members 14 to be affixed to one another so as to allow for easy biasing of the barrier member 12, while still allowing the central portion of the barrier member 12 to be uncovered.

It will also be noted from the figure that the central portion of the barrier member 12 is configured as a reservoir 34 adapted to hold a medicinal compound such as a spermicide or a therapeutic agent therein. While such agents may be utilized in conjunction with a device as shown in FIG. 1, the inclusion of a large reservoir 34 allows for higher capacity of such agents. It will also be noted that the device 30, includes a handle 36, formed from a loop of flexible material such as a polymeric fiber or the like, and to facilitate removal of the contraceptive device 30 from the vagina. As depicted, the handle 36 is attached to the ring 32 and it will appreciated that by pulling upon the handle, the device 30 is collapsed to its closed shape for withdrawal. Obviously, other such handle configurations may be similarly employed.

Figure 5:
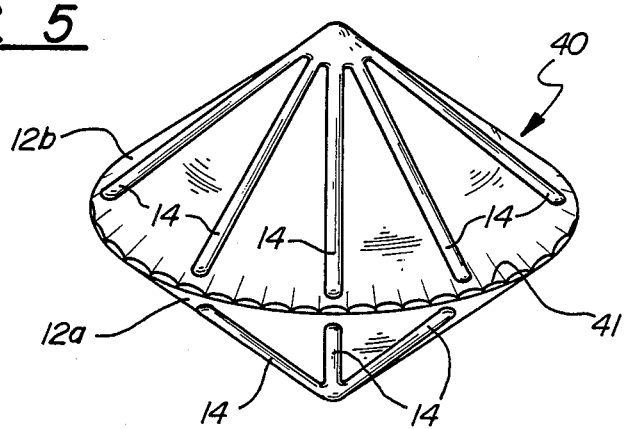
FIG. 5 is a perspective view of another barrier contraceptive device structured in accord with the principles of the present invention.

Referring now to FIG. 5 there is shown yet another configuration of device as structued in accord with the principles disclosed herein. The barrier contraceptive device 40 illustrated in FIG. 5 is fabricated by affixing two flexible, generally conical barrier members 12a, 12b along at least a portion of the perimeters thereof. It is generally preferred that at least one of the two barrier members 12a, 12b have stiffening members associated therewith and as illustrated both barrier members 12a, 12b have stiffening members 14 associated therewith.

As shown in the figure, the two barrier 12a, 12b are affixed to one another along a plurality of points on the perimeters thereof so as to define a number of openings 41. A device in this configuration is readily adapted to retain therein a relatively large amount of spermicide or other medicinal compound and furthermore, is capable of providing a relatively tight seat to the vaginal walls during use. The plurality of openings 41 allow for escape of spermicidal compounds therefrom so as to further complete the seal. The device 40 of FIG. 5 is also capable of folding into a fusiform shape for insertion and folding may be accomplished by either moving the apices of the two conical barrier members 12a, 12b in opposite directions from one another so as to provide a elongated, folded device or by moving the two apices together so as to fold one conical member inside the other.

Figure 7:
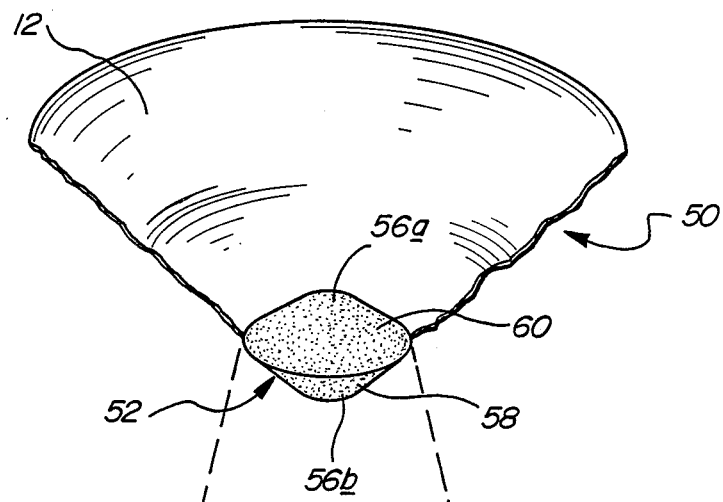
FIG. 7 is a cut-away view of a barrier contraceptive of the present invention as adapted to release a medicinal compound.

As was mentioned previously, the device of the present invention may be further adapted to release a medicated compound into the vagina. Referring now to FIG. 7, there is shown one such adaption. The device 50 of FIG. 7 includes a flexible barrier member 12 as shown previously. The stiffening members are not visible in this cut-away view. Also included is a medication releasing capsule 52 adapted to retain and release a medicinal compound such as a contraceptive or therapeutic agent.

Figure 8:
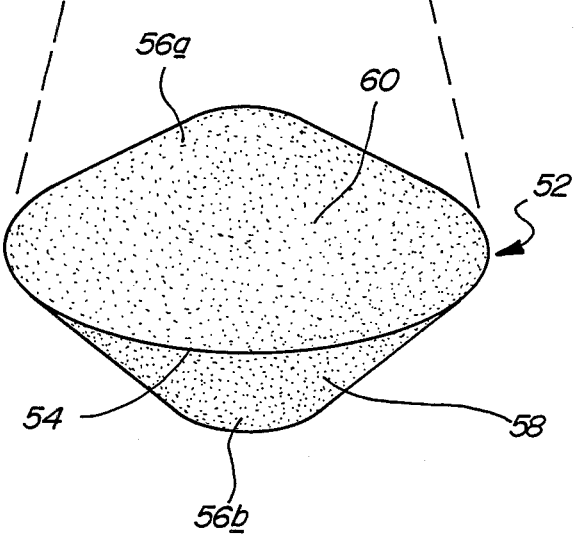
FIG. 8 is a perspective view of the medicinal compound containing a capsule of the barrier contraceptive of FIG. 7.

The capsule 52 which is shown in enlarged detail in FIG. 8, includes an upper 56a and lower 56b membrane adapted to release the medicinal compound from the regions 60, 58 bounded thereby. The capsule further includes an impervious barrier layer 54 extending thereacross and generally contiguous with the flexible barrier 12. The barrier layer 54 and flexible barrier 12 cooperates to provide a contraceptive shield.

The barrier layer 54 divides the capsule 52 into two compartments 58 and 60 bounded by the porous membranes 56a, 56b. Each compartment is adapted to store and release a medicinal agent; and accordingly, the capsule can accommodate a spermicide and a therapeutic agent. The membrane 56a, 56b can be porous polymeric materials, perforated materials and the like.

In one embodiment, the capsule 52 can be fabricated from a foam-like material impregnated with a spermicide and in that sense is similar to presently utilized contraceptive sponge. Such an embodiment would combine the advantages of the contraceptive sponge with those of the flexible umbrella-like device disclosed hereinabove.

Figure 9A:
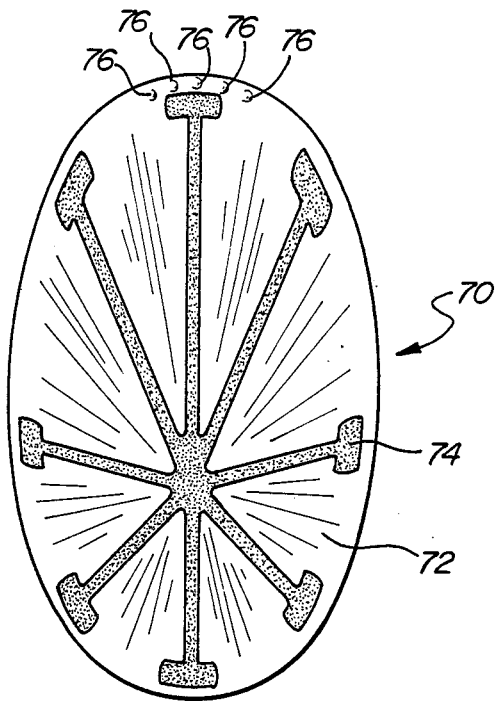
FIG. 9A is a top plan view of still another barrier contraceptive device of the instant invention.
Figure 9B:
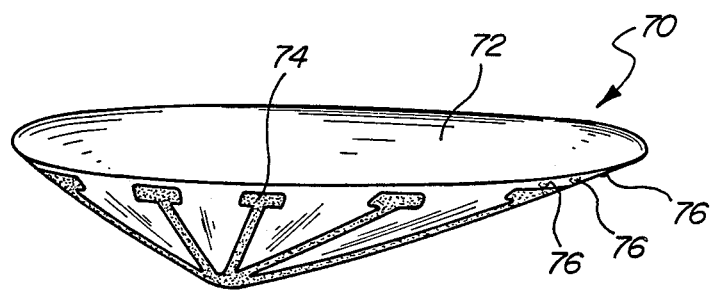
FIG. 9B is a side view, in perspective of the device of FIG. 9A.

Referring now to FIGS. 9A and 9B there is illustrated yet another barrier contraceptive structured in accord with the principles of the present invention. The device 70 is generally similar to those previously described insofar as it includes a flexible barrier member 72 and a plurality of stiffening members 74 affixed at a common locus and adapted to maintain the barrier member 70 in a generally planar configuration. Where the device 70 of this embodiment differs from those previously discussed is in that the barrier member 72 is of a generally oval shape. It will be noted from the figure that the central locus of the stiffening member 74 is not placed in the center of the oval barrier member 72, but is placed in an eccentric location. Such placement gives an overall irregular shape to the device 70, best seen in FIG. 9B, which is a side perspective view of the device. It will be noted that the eccentric placement of the stiffening member 74 serves to create an asymmetric profile to the device 70 such that a forward larger portion and a rearward smaller portion are defined.

In use, the contraceptive device 70 is inserted into the vagina proximate the cervix such that the larger or forward portion is disposed toward the ventral side of the body and the rearmost portion toward the dorsal side. It has been found that such configuration and disposition optimizes cervical shielding. It should be noted that while the placement of the stiffening members 74 is depicted as being eccentric to the barrier member 72, it may in some instances be advantageous to place the stiffening members in a central location in conjunction with an oval barrier member. In other instances, an eccentrically configured set of stiffening members can be employed in conjunction with a generally circular barrier member to create an asymmetrically profiled device.

In general, the size of the device 70 of FIGS. 9A, 9B is similar to that of the circular devices, i.e., a diameter of 50-95 millimeters will generally encompass all required sizes. In the instance of the oval device both the major diameter and the minor diameter thereof, as measured along a central axis will each be within the stated range.

The device 70 of FIGS. 9A, 9B illustrates another feature of the present invention. Problemsmay occur in user verification of the location of the contraceptive device, insofar as the barrier member 72 is relatively thin, particularly at the periphery thereof and accordingly it would be desirable to have some means for verifying the location of that periphery to assure proper device placement. Toward that end, the device 70 of FIG. 9A, 9B includes a plurality of molded in raised dots or bumps 76 along a portion of one rim thereof. These dots 76 provide a tactile contrast to the relatively thin barrier member 72 enabling the user to verify location of the upper rim. Obviously, other configurations such has a single dot, a raised bar or the like may be employed for this purpose. In the instance of a symmetrical (i.e., circular) type of device it may be desirable to place the tactile indicia along the entirety of the rim; however, in the instance of the asymmetric device 70 it will generally be preferred to place such indicia along only one end thereof so as to verify proper orientation of the device 70 as well as proper placement thereof.

Figure 10:
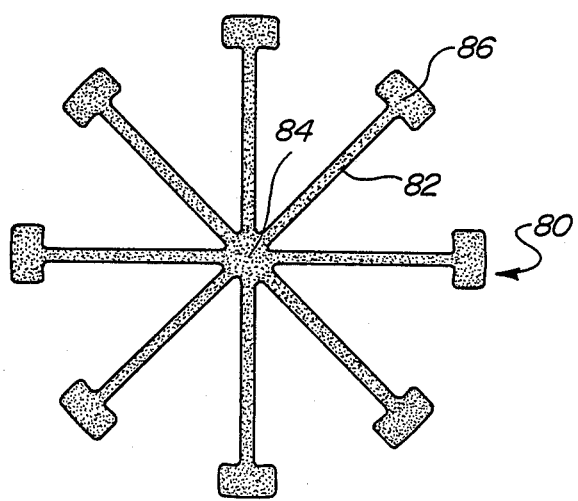
FIG. 10 is a top plan view of one particular design of stiffening member adapted for use in the present invention.

Referring now to FIG. 10 there is shown a top plan view of one particular configuration of stiffening member 80, structured in accord with the principles of the instant invention. As illustrated, this stiffening member includes individual arms 82 joined at a central locus 84, each of the arms 82 terminating in a tab portion 86. It has been found that the tab portions 86 serve to better anchor the barrier member and to maintain proper orientation thereof. The stiffening member 80 may be fabricated from any of the materials previously described and it has been found particularly advantageous to employ the block copolymer type materials previously referred to. It has also been found that it is desirable to provide a radial thickness profile to the stiffening member 80 such that the central locus 84 is relatively thick whereas the tabular portions 86 and the extremities of the arms 82 proximate thereto are relatively thin. In this manner, flexibility of the rim of the completed device is assured and proper fit readily obtained. Typically the central portion 84 will be from 1-5 mm in thickness, while the tabular portions 86 will be from 0.25-3 mm thick. However, the specific thicknesses will depend upon the resiliency of the material from which the member 80 is fabricated.

Obviously other variations of the stiffening member 80 of FIG. 10 may be employed. For example, and as previously discussed the central focus 84 may be replaced with a ringlike open structure. Also, a larger or smaller number of arms 82 may be included and, as illustrated with reference to the device of FIGS. 9A and 9B, the stiffening member 80 may have its central locus 84 disposed eccentric to the arms 82, which will then be of differing lengths and angular relationships. In those instances where the stiffening member 80 and the barrier member to which it attaches are fabricated from the same material they may be readily attached by a thermal lamination process. In other instances adhesive bonding may be employed.

Various other modifications of the depicted devices are possible within the scope of the present invention. For example, the stiffening members may not be separate members but may be provided by merely thickening a portion of the barrier member 12 so as to provide sufficient support and biasing force to enable proper function of the device. In another embodiment, the entire carrier member 12 may be fabricated from a porous or absorbent material adapted to retain and release spermicide or other medicinal compounds.

The umbrella-like barrier contraceptives of the present invention may be packaged for use as a single service item in a form preloaded with spermicidal compounds. Similarly, when the device is utilized as a delivery agent for chemotherapeutic compounds it may be dispensed with the therapeutic agent already in place. These and other modifications will be readily apparent to one of skill in the art and accordingly the foregoing drawings, discussion and description are merely meant to be illustrative of particular embodiments of the present invention and not limitations upon the practice thereof. It is the following claims, including all equivalents which define the scope of the instant invention.

I claim:

1. An intravaginal barrier type contraceptive device comprising two flexible, continuous, impermeable, generally conical barrier members each having a circular perimeter and an apex, said members joined at a plurality of points along said circular perimeters, with the apices oriented in opposite directions; each barrier member including a plurality of radially disposed, resilient stiffener members associated therewith, said stiffening members adapted to bias the barrier members into a generally conical configuration to uniformly contact the vaginal wall and form a tight barrier seal therewith, and having sufficient flexibility to allow said device to be folded into a generally fusiform shape for insertion and removal.

* * * * *